United States Patent
Tran

(10) Patent No.: US 12,232,910 B2
(45) Date of Patent: Feb. 25, 2025

(54) ULTRASOUND PROBE WITH PRESSURE MEASUREMENT CAPABILITY

(71) Applicant: Bard Access Systems, Inc., Salt Lake City, UT (US)

(72) Inventor: Huy Ngoc Tran, Riverton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/471,015

(22) Filed: Sep. 9, 2021

(65) Prior Publication Data
US 2022/0071593 A1 Mar. 10, 2022

Related U.S. Application Data

(60) Provisional application No. 63/076,589, filed on Sep. 10, 2020.

(51) Int. Cl.
*A61B 8/00* (2006.01)
*A61B 8/08* (2006.01)

(52) U.S. Cl.
CPC .......... *A61B 8/4444* (2013.01); *A61B 8/0841* (2013.01); *A61B 8/085* (2013.01); *A61B 8/463* (2013.01)

(58) Field of Classification Search
CPC ..... A61B 8/4444; A61B 8/0841; A61B 8/085; A61B 8/463; A61B 8/0891; A61B 8/4254
See application file for complete search history.

(56) References Cited

U.S. PATENT DOCUMENTS 3,697,917 A * 10/1972 Orth .................... G01L 19/0084
338/3
5,148,809 A 9/1992 Biegeleisen-Knight et al.
(Continued)

FOREIGN PATENT DOCUMENTS

CN 102871645 A 1/2013
CN 105107067 B 5/2018
(Continued)

OTHER PUBLICATIONS

PCT/US12/61182 International Seach Report and Written Opinion dated Mar. 11, 2013.
(Continued)

*Primary Examiner* — Sanjay Cattungal
(74) *Attorney, Agent, or Firm* — Rutan & Tucker LLP

(57) ABSTRACT

Disclosed herein are ultrasound probes, ultrasound systems, and ultrasound methods with pressure measurement capabilities for detecting and determining if bodily tissue is over-compressed during ultrasound imaging procedure. For example, an ultrasound probe can include a probe body, an articulating probe head attached to the probe body, and a pressure-sensing device housed in an articulating area between the articulating probe head and the probe body. In another example, a method of the ultrasound probe includes placing the articulating probe head of the ultrasound probe on a skin surface of a patient and moving the articulating probe head of the ultrasound probe over the patient while ultrasound signals are emitted into the patient from the articulating probe head for ultrasound imaging. The method also includes monitoring for any measured pressure values induced on the patient by the articulating probe head of the ultrasound probe in excess of a threshold pressure value.

22 Claims, 8 Drawing Sheets

(56) References Cited

U.S. PATENT DOCUMENTS

| | | |
|---|---|---|
| 5,181,513 A | 1/1993 | Touboul et al. |
| 5,325,293 A | 6/1994 | Dorne |
| 5,349,865 A * | 9/1994 | Kavli .................. G01L 9/0072 |
| | | 361/283.4 |
| 5,441,052 A | 8/1995 | Miyajima |
| 5,549,554 A | 8/1996 | Miraki |
| 5,573,529 A | 11/1996 | Haak et al. |
| 5,758,650 A | 6/1998 | Miller et al. |
| 5,775,322 A | 7/1998 | Silverstein et al. |
| 5,879,297 A | 3/1999 | Haynor et al. |
| 5,897,503 A * | 4/1999 | Lyon ....................... A61B 8/00 |
| | | 600/459 |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,733,458 B1 | 5/2004 | Steins et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,038,619 B2 * | 10/2011 | Steinbacher ........... A61B 8/467 |
| | | 600/459 |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,336,536 B1 | 12/2012 | Wood-Putnam et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,087,147 B1 | 7/2015 | Fonte |
| 9,138,290 B2 | 9/2015 | Hadjicostis |
| 9,199,082 B1 | 12/2015 | Yared et al. |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |
| 11,564,861 B1 * | 1/2023 | Gaines .................. A61H 23/04 |
| 11,900,593 B2 | 2/2024 | Dhatt et al. |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2003/0125629 A1 | 7/2003 | Ustuner |
| 2003/0135115 A1 | 7/2003 | Burdette et al. |
| 2003/0149366 A1 | 8/2003 | Stringer et al. |
| 2004/0015080 A1 * | 1/2004 | Kelly .................... A61B 8/406 |
| | | 600/459 |
| 2004/0055925 A1 | 3/2004 | Franks-Farah et al. |
| 2004/0197267 A1 | 10/2004 | Black et al. |
| 2005/0000975 A1 | 1/2005 | Carco et al. |
| 2005/0049504 A1 | 3/2005 | Lo et al. |

(56) References Cited

U.S. PATENT DOCUMENTS

| | | |
|---|---|---|
| 2005/0075597 A1 | 4/2005 | Vournakis et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0004290 A1* | 1/2006 | Smith .................... G01S 15/899 600/459 |
| 2006/0013523 A1 | 1/2006 | Childers et al. |
| 2006/0015039 A1 | 1/2006 | Cassidy et al. |
| 2006/0020204 A1 | 1/2006 | Serra et al. |
| 2006/0047617 A1 | 3/2006 | Bacioiu et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2006/0241463 A1 | 10/2006 | Shau et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1 | 7/2007 | Timinger et al. |
| 2007/0199848 A1 | 8/2007 | Ellswood et al. |
| 2007/0239005 A1 | 10/2007 | Ogasawara |
| 2007/0239120 A1 | 10/2007 | Brock et al. |
| 2007/0249911 A1 | 10/2007 | Simon |
| 2007/0287886 A1 | 12/2007 | Saadat |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0269605 A1 | 10/2008 | Nakaya |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1* | 1/2009 | Steinbacher ............ A61B 8/467 600/459 |
| 2009/0074280 A1 | 3/2009 | Lu et al. |
| 2009/0124903 A1* | 5/2009 | Osaka .................... A61B 8/485 600/443 |
| 2009/0137887 A1 | 5/2009 | Shariati et al. |
| 2009/0137907 A1 | 5/2009 | Takimoto et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1 | 11/2009 | Boyden et al. |
| 2009/0306509 A1 | 12/2009 | Pedersen et al. |
| 2010/0010348 A1 | 1/2010 | Halmann |
| 2010/0168576 A1 | 7/2010 | Poland et al. |
| 2010/0211026 A2 | 8/2010 | Sheetz et al. |
| 2010/0249598 A1* | 9/2010 | Smith .................... A61B 8/4455 600/459 |
| 2010/0286515 A1 | 11/2010 | Gravenstein et al. |
| 2010/0312121 A1 | 12/2010 | Guan |
| 2010/0324423 A1* | 12/2010 | El-Aklouk ............ A61B 8/4488 600/444 |
| 2011/0002518 A1 | 1/2011 | Ziv-Ari et al. |
| 2011/0026796 A1 | 2/2011 | Hyun et al. |
| 2011/0071404 A1 | 3/2011 | Schmitt et al. |
| 2011/0074244 A1* | 3/2011 | Osawa .................... B06B 1/0622 310/318 |
| 2011/0087107 A1* | 4/2011 | Lindekugel .......... A61B 8/4455 600/459 |
| 2011/0166451 A1 | 7/2011 | Blaivas et al. |
| 2011/0282188 A1 | 11/2011 | Burnside et al. |
| 2011/0295108 A1* | 12/2011 | Cox ........................ A61B 5/339 600/424 |
| 2011/0313293 A1* | 12/2011 | Lindekugel ............ A61B 10/00 600/459 |
| 2012/0136242 A1 | 5/2012 | Qi et al. |
| 2012/0136256 A1 | 5/2012 | Nozaki et al. |
| 2012/0165679 A1* | 6/2012 | Orome .................. A61B 5/150748 600/461 |
| 2012/0179038 A1 | 7/2012 | Meurer et al. |
| 2012/0179042 A1 | 7/2012 | Fukumoto et al. |
| 2012/0179044 A1* | 7/2012 | Chiang .................... A61B 8/14 600/467 |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0144166 A1 | 6/2013 | Specht et al. |
| 2013/0150724 A1 | 6/2013 | Blaivas et al. |
| 2013/0188832 A1 | 7/2013 | Ma et al. |
| 2013/0197367 A1 | 8/2013 | Smok et al. |
| 2013/0218024 A1 | 8/2013 | Boctor et al. |
| 2013/0323700 A1 | 12/2013 | Samosky et al. |
| 2013/0338503 A1* | 12/2013 | Cohen .................... A61B 8/4411 600/443 |
| 2013/0338508 A1* | 12/2013 | Nakamura ............ A61B 8/4494 600/459 |
| 2013/0345566 A1 | 12/2013 | Weitzel et al. |
| 2014/0005530 A1 | 1/2014 | Liu et al. |
| 2014/0031694 A1* | 1/2014 | Solek .................... A61B 8/4427 600/459 |
| 2014/0066779 A1* | 3/2014 | Nakanishi ............ A61B 8/4444 600/459 |
| 2014/0073976 A1 | 3/2014 | Fonte et al. |
| 2014/0100440 A1 | 4/2014 | Cheline et al. |
| 2014/0114194 A1* | 4/2014 | Kanayama ............ A61B 8/4254 600/459 |
| 2014/0170620 A1 | 6/2014 | Savitsky et al. |
| 2014/0180098 A1 | 6/2014 | Flaherty et al. |
| 2014/0180116 A1* | 6/2014 | Lindekugel .......... A61B 8/4455 600/459 |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1* | 9/2014 | Amble .................. A61B 8/4488 600/447 |
| 2014/0276081 A1 | 9/2014 | Tegels |
| 2014/0276085 A1 | 9/2014 | Miller |
| 2014/0276690 A1 | 9/2014 | Grace |
| 2014/0296694 A1 | 10/2014 | Jaworski |
| 2014/0343431 A1 | 11/2014 | Vajinepalli et al. |
| 2014/0357994 A1* | 12/2014 | Jin ........................ A61B 8/485 600/438 |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0141821 A1 | 5/2015 | Yoshikawa et al. |
| 2015/0190111 A1 | 7/2015 | Fry |
| 2015/0209003 A1 | 7/2015 | Halmann et al. |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0245820 A1 | 9/2015 | Tamada |
| 2015/0257735 A1 | 9/2015 | Ball et al. |
| 2015/0272448 A1 | 10/2015 | Fonte et al. |
| 2015/0282890 A1 | 10/2015 | Cohen et al. |
| 2015/0294497 A1 | 10/2015 | Ng et al. |
| 2015/0297097 A1 | 10/2015 | Matsubara et al. |
| 2015/0342572 A1 | 12/2015 | Tahmasebi Maraghoosh et al. |
| 2015/0359520 A1* | 12/2015 | Shan .................... A61B 8/0858 600/443 |
| 2015/0359991 A1 | 12/2015 | Dunbar et al. |
| 2016/0000367 A1 | 1/2016 | Lyon |
| 2016/0000399 A1 | 1/2016 | Halmann et al. |
| 2016/0026894 A1* | 1/2016 | Nagase ................ A61B 8/4263 600/443 |
| 2016/0029995 A1 | 2/2016 | Navratil et al. |
| 2016/0038119 A1 | 2/2016 | Desjardins |
| 2016/0081674 A1 | 3/2016 | Bagwan et al. |
| 2016/0113517 A1 | 4/2016 | Lee et al. |
| 2016/0113699 A1 | 4/2016 | Sverdlik et al. |
| 2016/0120607 A1 | 5/2016 | Sorotzkin et al. |

(56) References Cited

U.S. PATENT DOCUMENTS

| | | |
|---|---|---|
| 2016/0125639 A1 | 5/2016 | Park et al. |
| 2016/0157831 A1 | 6/2016 | Kang et al. |
| 2016/0166232 A1 | 6/2016 | Merritt |
| 2016/0202053 A1 | 7/2016 | Walker et al. |
| 2016/0211045 A1 | 7/2016 | Jeon et al. |
| 2016/0213398 A1 | 7/2016 | Liu |
| 2016/0220124 A1 | 8/2016 | Grady et al. |
| 2016/0259992 A1 | 9/2016 | Knodt et al. |
| 2016/0278869 A1 | 9/2016 | Grunwald |
| 2016/0287214 A1 | 10/2016 | Ralovich et al. |
| 2016/0296208 A1 | 10/2016 | Sethuraman et al. |
| 2016/0374644 A1 | 12/2016 | Mauldin, Jr. et al. |
| 2017/0014105 A1 | 1/2017 | Chono |
| 2017/0020561 A1 | 1/2017 | Cox et al. |
| 2017/0079548 A1 | 3/2017 | Silverstein et al. |
| 2017/0086785 A1 | 3/2017 | Bjaerum |
| 2017/0103534 A1 | 4/2017 | Park et al. |
| 2017/0143312 A1 | 5/2017 | Hedlund et al. |
| 2017/0164923 A1 | 6/2017 | Matsumoto |
| 2017/0172666 A1* | 6/2017 | Govari ............... A61B 18/1492 |
| 2017/0215842 A1 | 8/2017 | Ryu et al. |
| 2017/0252004 A1 | 9/2017 | Broad et al. |
| 2017/0258522 A1 | 9/2017 | Goshgarian et al. |
| 2017/0328751 A1* | 11/2017 | Lemke .................... G01H 9/00 |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0235649 A1 | 8/2018 | Elkadi |
| 2018/0235709 A1 | 8/2018 | Donhowe et al. |
| 2018/0289927 A1 | 10/2018 | Messerly |
| 2018/0296185 A1 | 10/2018 | Cox et al. |
| 2018/0310955 A1 | 11/2018 | Lindekugel et al. |
| 2018/0333135 A1 | 11/2018 | Kim et al. |
| 2018/0344293 A1 | 12/2018 | Raju et al. |
| 2019/0029636 A1 | 1/2019 | Lee et al. |
| 2019/0060001 A1 | 2/2019 | Kohli et al. |
| 2019/0060014 A1 | 2/2019 | Hazelton et al. |
| 2019/0090855 A1 | 3/2019 | Kobayashi et al. |
| 2019/0125210 A1 | 5/2019 | Govari et al. |
| 2019/0200951 A1 | 7/2019 | Meier |
| 2019/0239848 A1 | 8/2019 | Bedi et al. |
| 2019/0239850 A1 | 8/2019 | Dalvin et al. |
| 2019/0307419 A1 | 10/2019 | Durfee |
| 2019/0307515 A1 | 10/2019 | Naito et al. |
| 2019/0307516 A1 | 10/2019 | Schotzko et al. |
| 2019/0365347 A1 | 12/2019 | Abe |
| 2019/0365348 A1 | 12/2019 | Toume et al. |
| 2019/0365354 A1 | 12/2019 | Du |
| 2020/0069929 A1 | 3/2020 | Mason et al. |
| 2020/0113540 A1 | 4/2020 | Gijsbers et al. |
| 2020/0163654 A1* | 5/2020 | Satir .................... A61B 8/58 |
| 2020/0200900 A1 | 6/2020 | Asami et al. |
| 2020/0229795 A1 | 7/2020 | Tadross et al. |
| 2020/0230391 A1 | 7/2020 | Burkholz et al. |
| 2020/0237403 A1 | 7/2020 | Southard et al. |
| 2020/0281563 A1 | 9/2020 | Muller et al. |
| 2020/0359990 A1 | 11/2020 | Poland et al. |
| 2020/0390416 A1 | 12/2020 | Swan et al. |
| 2021/0059639 A1* | 3/2021 | Howell ................ A61B 8/4444 |
| 2021/0077058 A1 | 3/2021 | Mashood et al. |
| 2021/0137492 A1 | 5/2021 | Imai |
| 2021/0146167 A1 | 5/2021 | Barthe et al. |
| 2021/0161510 A1 | 6/2021 | Sasaki et al. |
| 2021/0186467 A1 | 6/2021 | Urabe et al. |
| 2021/0212668 A1* | 7/2021 | Li ...................... G01S 15/8995 |
| 2021/0267569 A1 | 9/2021 | Yamamoto |
| 2021/0267570 A1 | 9/2021 | Ulman et al. |
| 2021/0295048 A1 | 9/2021 | Buras et al. |
| 2021/0315538 A1 | 10/2021 | Brandl et al. |
| 2021/0373602 A1 | 12/2021 | Min |
| 2021/0378627 A1 | 12/2021 | Yarmush et al. |
| 2022/0019313 A1 | 1/2022 | He et al. |
| 2022/0022969 A1 | 1/2022 | Misener |
| 2022/0039777 A1 | 2/2022 | Durfee |
| 2022/0039829 A1 | 2/2022 | Zijlstra et al. |
| 2022/0071593 A1* | 3/2022 | Tran ...................... A61B 8/463 |
| 2022/0096053 A1 | 3/2022 | Sethuraman et al. |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0225963 A1 | 7/2022 | Sutton et al. |
| 2022/0296303 A1 | 9/2022 | McLeod et al. |
| 2022/0304652 A1 | 9/2022 | Peterson et al. |
| 2022/0330922 A1 | 10/2022 | Sowards et al. |
| 2022/0334251 A1 | 10/2022 | Sowards et al. |
| 2022/0361840 A1 | 11/2022 | Matsumoto et al. |
| 2023/0048327 A1 | 2/2023 | Lampe et al. |
| 2023/0107629 A1 | 4/2023 | Sowards et al. |
| 2023/0132148 A1 | 4/2023 | Sowards et al. |
| 2023/0135562 A1 | 5/2023 | Misener et al. |
| 2023/0135757 A1 | 5/2023 | Bauer et al. |
| 2023/0138970 A1 | 5/2023 | Sowards et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0338010 A1 | 10/2023 | Sturm |
| 2023/0371928 A1 | 11/2023 | Rajguru et al. |
| 2023/0397900 A1 | 12/2023 | Prince |
| 2024/0065673 A1 | 2/2024 | Sowards et al. |
| 2024/0307024 A1 | 9/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 2823766 A1 | 1/2015 |
| EP | 3181083 A1 | 6/2017 |
| EP | 3870059 | 9/2021 |
| JP | 2000271136 A | 10/2000 |
| JP | 2007222291 A | 9/2007 |
| JP | 2014150928 A | 8/2014 |
| JP | 2018175547 A | 11/2018 |
| KR | 20180070878 A | 6/2018 |
| KR | 102176196 B1 | 11/2020 |
| WO | 2004082749 A2 | 9/2004 |
| WO | 2007115174 A2 | 10/2007 |
| WO | 2010029521 A2 | 3/2010 |
| WO | 2010076808 A1 | 7/2010 |
| WO | 2013059714 A1 | 4/2013 |
| WO | 2014/115150 A1 | 7/2014 |
| WO | 2015/017270 A1 | 2/2015 |
| WO | 2016/081023 A1 | 5/2016 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020067897 A1 | 4/2020 |
| WO | 2020083660 A1 | 4/2020 |
| WO | 2020/186198 A1 | 9/2020 |
| WO | 2021123905 A2 | 6/2021 |
| WO | 2021198226 A1 | 10/2021 |
| WO | 2022072727 A2 | 4/2022 |
| WO | 2022/081904 A1 | 4/2022 |
| WO | 2022/119853 A1 | 6/2022 |
| WO | 2022115479 A1 | 6/2022 |
| WO | 2022119856 A1 | 6/2022 |
| WO | 2022/221703 A1 | 10/2022 |

(56) References Cited

FOREIGN PATENT DOCUMENTS

| WO | 2022/221714 A1 | 10/2022 |
|---|---|---|
| WO | 2023059512 A1 | 4/2023 |
| WO | 2023076268 A1 | 5/2023 |
| WO | 2023081220 A1 | 5/2023 |
| WO | 2023081223 A1 | 5/2023 |
| WO | 2023091424 A1 | 5/2023 |
| WO | 2023167866 A1 | 9/2023 |
| WO | 2023177718 A1 | 9/2023 |
| WO | 2024044277 A1 | 2/2024 |

OTHER PUBLICATIONS

PCT/US2021/049123 filed Sep. 3, 2021 International Search Report and Written Opinion dated Feb. 4, 2022.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
PCT/US2021/045218 filed Aug. 9, 2021 International Search Report and Written Opinion dated Nov. 23, 2021.
PCT/US2021/049123 filed Sep. 3, 2021 International Search Report and Written Opinion dated May 16, 2022.
PCT/US2021/053018 filed Sep. 30, 2021 International Search Report and Written Opinion dated May 3, 2022.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
U.S. Appl. No. 15/951,903, filed Apr. 12, 2018 Board Decision dated Apr. 20, 2022.
U.S. Appl. No. 15/951,903, filed Apr. 12, 2018 Notice of Allowance dated May 2, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US2022047727 filed Oct. 25, 2022 International Search Report and Written Opinion dated Jan. 25, 2023.
U.S. Appl. No. 17/020,476, filed Sep. 14, 2020 Final Office Action dated Jan. 5, 2023.
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2022/025082 filed Apr. 15, 2022 International Search Report and Written Opinion dated Jul. 11, 2022.
PCT/US2022/025097 filed Apr. 15, 2022 International Search Report and Written Opinion dated Jul. 8, 2022.
U.S. Appl. No. 17/020,476, filed Sep. 14, 2020 Advisory Action dated Aug. 19, 2022.
U.S. Appl. No. 17/020,476, filed Sep. 14, 2020 Final Office Action dated Jun. 9, 2022.
U.S. Appl. No. 17/020,476, filed Sep. 14, 2020 Non-Final Office Action dated Sep. 23, 2022.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022/049983 filed Nov. 15, 2022 International Search Report and Written Opinion dated Mar. 29, 2023.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. Appl. No. 17/534,099, filed Nov. 23, 2021 Non-Final Office Action dated Mar. 31, 2023.
U.S. Appl. No. 17/538,911, filed Nov. 30, 2021 Non-Final Office Action dated Mar. 2, 2023.
U.S. Appl. No. 17/684,180, filed Mar. 1, 2022 Restriction Requirement dated May 19, 2023.
EP 20866520.8 filed Apr. 5, 2022 Extended European Search Report dated Aug. 22, 2023.
U.S. Appl. No. 17/468,318, filed Sep. 7, 2021 Final Office Action dated Sep. 8, 2023.
U.S. Appl. No. 17/534,099, filed Nov. 23, 2021 Final Office Action dated Sep. 29, 2023.
U.S. Appl. No. 17/538,911, filed Nov. 30, 2021 Final Office Action dated Sep. 13, 2023.
U.S. Appl. No. 17/684,180, filed Mar. 1, 2022 Non-Final Office Action dated Jul. 28, 2023.
U.S. Appl. No. 17/722,151, filed Apr. 15, 2022 Non-Final Office Action dated Sep. 7, 2023.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/534,099, filed Nov. 23, 2021 Advisory Action dated Dec. 8, 2023.
U.S. Appl. No. 17/538,911, filed Nov. 30, 2021 Advisory Action dated Nov. 22, 2023.
U.S. Appl. No. 17/722,151, filed Apr. 15, 2022 Advisory Action dated Jan. 2, 2024.

(56) References Cited

OTHER PUBLICATIONS

U.S. Appl. No. 17/722,151, filed Apr. 15, 2022 Final Office Action dated Nov. 6, 2023.
U.S. Appl. No. 17/894,460, filed Aug. 24, 2022 Non-Final Office Action dated Nov. 6, 2023.
M. Ikhsan, K. K. Tan, AS. Putra, C. F. Kong, et. al., "Automatic identification of blood vessel cross-section for central venous catheter placement using a cascading classifier," 39th Annual International Conference of the IEEE Engineering in Medicine and Biology Society (EMBC).pp. 1489-1492 (Year: 2017).
U.S. Appl. No. 17/468,318, filed Sep. 7, 2021 Notice of Allowance dated Jan. 18, 2024.
U.S. Appl. No. 17/534,099, filed Nov. 23, 2021 Non-Final Office Action dated Mar. 14, 2024.
U.S. Appl. No. 17/538,911, filed Nov. 30, 2021 Notice of Allowance dated Mar. 14, 2024.
U.S. Appl. No. 17/538,943, filed Nov. 30, 2021 Non-Final Office Action dated Jan. 30, 2024.
U.S. Appl. No. 17/684,180, filed Mar. 1, 2022 Final Office Action dated Jan. 18, 2024.
U.S. Appl. No. 17/722,111, filed Apr. 15, 2022 Non-Final Office Action dated Dec. 22, 2023.
U.S. Appl. No. 17/894,460, filed Aug. 24, 2022 Final Office Action dated Jan. 31, 2024.
U.S. Appl. No. 17/684,180, filed Mar. 1, 2022 Advisory Action dated Apr. 4, 2024.
U.S. Appl. No. 17/684,180, filed Mar. 1, 2022 Non-Final Office Action dated May 8, 2024.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/979,564, filed Nov. 2, 2022 Non-Final Office Action dated Jun. 5, 2024.
U.S. Appl. No. 18/238,281, filed Aug. 25, 2023 Non-Final Office Action dated Mar. 22, 2024.
PCT/US2022/045372 filed Sep. 30, 2022 International Search Report and Written Opinion dated Jan. 14, 2023.
Thermographic venous blood flow characterization with external cooling stimulation (Year: 2018).
U.S. Appl. No. 17/534,099, filed Nov. 23, 2021 Notice of Allowance dated Sep. 18, 2024.
U.S. Appl. No. 17/538,943, filed Nov. 30, 2021 Notice of Allowance dated Aug. 14, 2024.
U.S. Appl. No. 17/684,180, filed Mar. 1, 2022 Final Office Action dated Sep. 23, 2024.
U.S. Appl. No. 17/722,111, filed Apr. 15, 2022 Final Office Action dated Jul. 12, 2024.
U.S. Appl. No. 17/722,151, filed Apr. 15, 2022 Final Office Action dated Sep. 20, 2024.
U.S. Appl. No. 17/894,460, filed Aug. 24, 2022 Non-Final Office Action dated Sep. 25, 2024.
U.S. Appl. No. 17/957,562, filed Sep. 30, 2022 Non-Final Office Action dated Jun. 20, 2024.
U.S. Appl. No. 17/979,601, filed Nov. 2, 2022 Non-Final Office Action dated Aug. 20, 2024.
U.S. Appl. No. 17/987,698, filed Nov. 15, 2022 Non-Final Office Action dated Sep. 20, 2024.
U.S. Appl. No. 18/238,281, filed Aug. 25, 2023 Notice of Allowance dated Jul. 16, 2024.
PCT/US2024/037647 filed Jul. 11, 2024 International Search Report and Written Opinion dated Oct. 16, 2024.
U.S. Appl. No. 17/684,180 filed Mar. 1, 2022 Advisory Action dated Dec. 27, 2024.
U.S. Appl. No. 17/722,111 filed Apr. 15, 2022 Advisory Action dated Oct. 23, 2024.
U.S. Appl. No. 17/722,111, filed Apr. 15, 2022 Notice of Allowance dated Dec. 18, 2024.
U.S. Appl. No. 17/722,151 filed Apr. 15, 2022 Advisory Action dated Dec. 27, 2024.
U.S. Appl. No. 17/894,460, filed Aug. 24, 2022 Final Office Action dated Dec. 31, 2024.
U.S. Appl. No. 17/957,562, filed Sep. 30, 2022 Final Office Action dated Nov. 27, 2024.
U.S. Appl. No. 17/973,171 filed Oct. 25, 2022 Non-Final Office Action dated Dec. 6, 2024.
U.S. Appl. No. 17/979,564, filed Nov. 2, 2022 Final Office Action dated Oct. 18, 2024.
U.S. Appl. No. 17/979,601, filed Nov. 2, 2022 Final Office Action dated Dec. 5, 2024.
U.S. Appl. No. 17/987,698, filed Nov. 15, 2022 Final Office Action dated Dec. 13, 2024.
U.S. Appl. No. 18/113,003, filed Feb. 22, 2023 Non-Final Office Action dated Nov. 27, 2024.
U.S. Appl. No. 18/121,802, filed Mar. 15, 2023 Non-Final Office Action dated Dec. 16, 2024.

* cited by examiner

ULTRASOUND PROBE WITH PRESSURE MEASUREMENT CAPABILITY

PRIORITY

This application claims the benefit of priority to U.S. Provisional Application No. 63/076,589, filed Sep. 10, 2020, which is incorporated by reference in its entirety into this application.

BACKGROUND

There are currently a variety of existing ultrasound systems including wired or wireless ultrasound probes that connect to displays. These systems can be used by clinicians for assessing a site such as a blood vessel for placing a vascular access device ("VAD") including a catheter. These systems can also by clinicians for assessing placement of the VAD or catheter at a chosen site. However, bodily tissue of a patient can be appreciably compressed while assessing such sites by simply using the ultrasound probes as intended. Compression of the bodily tissue can compromise vessel purchase by the VAD or catheter, which, in turn, can result in catheter extravasation that can be dangerous to the patient's health. Existing ultrasound systems do not provide for measuring bodily tissue-compressing pressure caused by the ultrasound probes during ultrasound imaging.

Disclosed herein are ultrasound probes, ultrasound systems, and ultrasound methods with pressure measurement capabilities for detecting and determining if bodily tissue is over-compressed during ultrasound imaging.

SUMMARY

Disclosed herein is an ultrasound probe including, in some embodiments, a probe body, an articulating probe head attached to the probe body, and a pressure-sensing device housed in an articulating area between the articulating probe head and the probe body.

In some embodiments, the ultrasound probe further includes a boot connecting the articulating probe head to the probe body in the articulating area. The boot is configured to cover or incorporate therein the pressure-sensing device.

In some embodiments, the pressure-sensing device is configured to detect deformations in or around an elastic material of the boot. The deformations are induced by pressing the articulating probe head into a patient.

In some embodiments, the pressure-sensing device is communicatively coupled to a controller of the ultrasound probe. The controller is configured to convert electrical signals corresponding to the deformations into measured pressure values.

In some embodiments, the ultrasound probe is configured to provide the measured pressure values to a display to be displayed to a clinician.

In some embodiments, the ultrasound probe includes logic configured to compare a measured pressure value against a threshold pressure value.

In some embodiments, the ultrasound probe includes a speaker configured to emit an audio signal to alert a clinician when the measured pressure value exceeds the threshold pressure value.

In some embodiments, the ultrasound probe includes a light-emitting diode configured to emit a visual signal to alert a clinician when the measured pressure value exceeds the threshold pressure value.

In some embodiments, the pressure-sensing device is a pressure transducer.

In some embodiments, the pressure transducer is a piezoresistive strain-gauge pressure transducer. The pressure transducer includes a strain gauge bonded to a flexible diaphragm in the articulating area between the articulating probe head and the probe body. A deformation in the diaphragm provides a corresponding measurable change in strain-gauge electrical resistance indicative of the pressure induced by pressing the articulating probe head into a patient to cause the deformation.

In some embodiments, the pressure transducer is a variable capacitance pressure transducer. The pressure transducer includes a diaphragm electrode and an opposing electrode in the articulating area between the articulating probe head and the probe body. A deformation in a flexible diaphragm affects a distance between the diaphragm electrode and the opposing electrode providing a corresponding measurable change in capacitance indicative of the pressure induced by pressing the articulating probe head into a patient to cause the deformation.

Also disclosed herein is an ultrasound system including, in some embodiments, a console and an ultrasound probe. The console includes a display configured for rendering ultrasound images on a display screen of the display. The ultrasound probe includes a probe body, an articulating probe head attached to the probe body, and a pressure-sensing device housed in an articulating area between the articulating probe head and the probe body.

In some embodiments, the ultrasound probe further includes a boot connecting the articulating probe head to the probe body in the articulating area. The boot is configured to cover or incorporate therein the pressure-sensing device.

In some embodiments, the pressure-sensing device is configured to detect deformations in or around an elastic material of the boot. The deformations are induced by pressing the articulating probe head into a patient.

In some embodiments, the pressure-sensing device is communicatively coupled to a controller of the console. The controller is configured to convert electrical signals corresponding to the deformations into measured pressure values.

In some embodiments, the ultrasound probe is configured to provide the measured pressure values to the display to be displayed to a clinician.

In some embodiments, the console includes logic configured to compare a measured pressure value against a threshold pressure value.

In some embodiments, the console includes a speaker configured to emit an audio signal to alert a clinician when the measured pressure value exceeds the threshold pressure value.

In some embodiments, the display is configured to emit a visual signal to alert a clinician when the measured pressure value exceeds the threshold pressure value.

In some embodiments, the display is configured to display visual feedback including a visualization of a target vein and a catheter placed in the target vein.

In some embodiments, the pressure-sensing device is a piezoresistive strain-gauge pressure transducer. The pressure transducer includes a strain gauge bonded to a flexible diaphragm in the articulating area between the articulating probe head and the probe body. A deformation in the diaphragm provides a corresponding measurable change in strain-gauge electrical resistance indicative of the pressure induced by pressing the articulating probe head into a patient to cause the deformation.

In some embodiments, the pressure-sensing device is a variable capacitance pressure transducer. The pressure transducer includes a diaphragm electrode and an opposing electrode in the articulating area between the articulating probe head and the probe body. A deformation in a flexible diaphragm affecting a distance between the diaphragm electrode and the opposing electrode providing a corresponding measurable change in capacitance indicative of the pressure induced by pressing the articulating probe head into a patient to cause the deformation.

Also disclosed herein is a method of an ultrasound system including, in some embodiments, an ultrasound probe-obtaining step, an ultrasound probe-placing step, an ultrasound probe-moving step, and a pressure-monitoring step. The ultrasound probe-obtaining step includes obtaining the ultrasound probe. The ultrasound probe includes a probe body, an articulating probe head attached to the probe body, and a pressure-sensing device housed in an articulating area between the articulating probe head and the probe body. The ultrasound probe-placing step includes placing the articulating probe head of the ultrasound probe on a skin surface of a patient. The ultrasound probe-moving step includes moving the articulating probe head of the ultrasound probe over the patient while ultrasound signals are emitted into the patient from the articulating probe head for ultrasound imaging. The pressure-monitoring step includes monitoring for any measured pressure values induced on the patient by the articulating probe head of the ultrasound probe in excess of a threshold pressure value.

In some embodiments, the pressure-monitoring step includes viewing the measured pressure values on a display screen of a display.

In some embodiments, the pressure-monitoring step includes monitoring for a visual signal on the display screen of the display that alerts a clinician when any measured pressure values are in excess of the threshold pressure value.

In some embodiments, the pressure-monitoring step includes monitoring for an audio signal that alerts a clinician when any measured pressure values are in excess of the threshold pressure value.

In some embodiments, the method further includes a catheter placement-adjusting step. The catheter placement-adjusting step includes adjusting catheter placement responsive to any measured pressure values in excess of the threshold pressure value to ensure a sufficient blood-vessel purchase that minimizes catheter extravasation.

These and other features of the concepts provided herein will become more apparent to those of skill in the art in view of the accompanying drawings and following description, which describe particular embodiments of such concepts in greater detail.

DRAWINGS

DESCRIPTION

Figure 2:
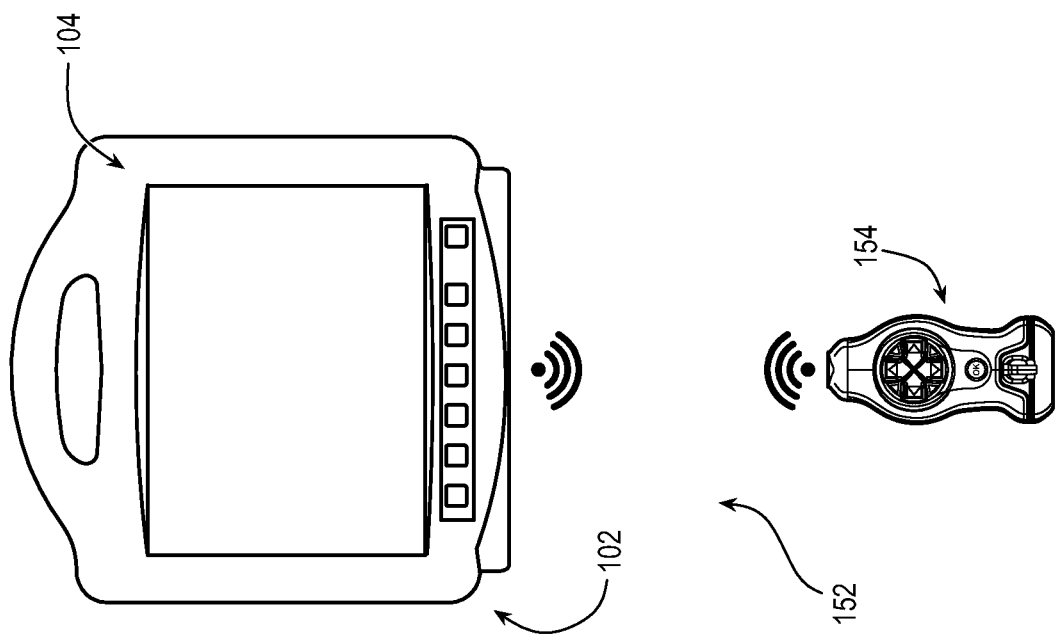
FIG. 2 illustrates a wireless ultrasound system including a console and an ultrasound probe in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

As set forth above, existing ultrasound systems do not provide for measuring bodily tissue-compressing pressure caused by ultrasound probes during ultrasound imaging. Disclosed herein are ultrasound probes, ultrasound systems, and ultrasound methods with pressure measurement capabilities for detecting and determining if bodily tissue is over-compressed during ultrasound imaging.

Ultrasound Systems

Figure 1:
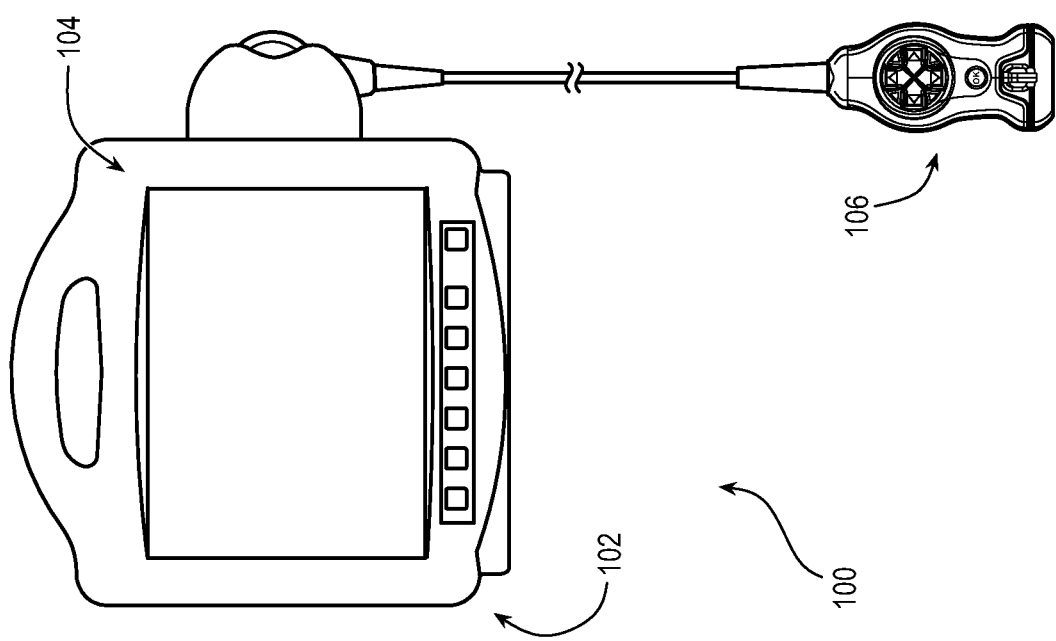
FIG. 1 illustrates a wired ultrasound system including a console and an ultrasound probe in accordance with some embodiments.
Figure 3:
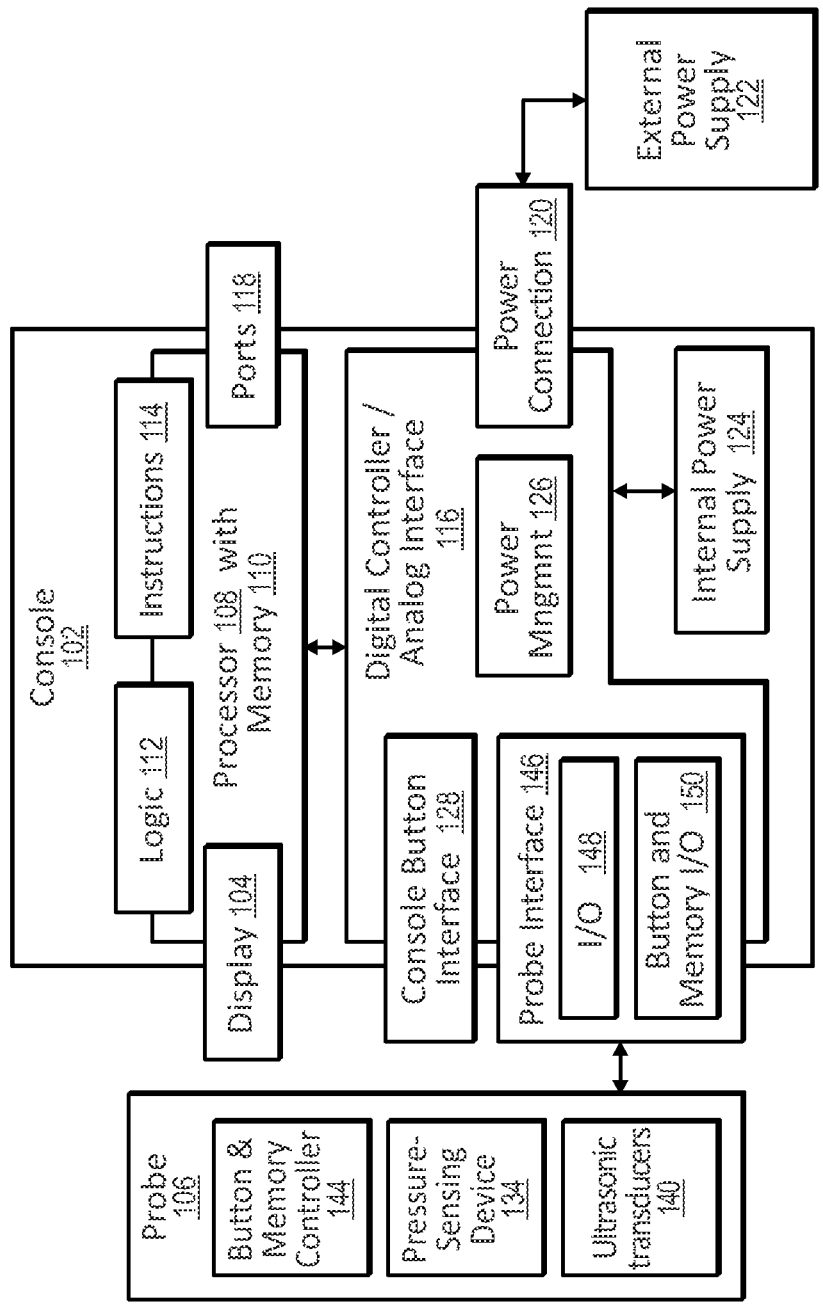
FIG. 3 illustrates a block diagram of the ultrasound system of FIG. 1 in accordance with some embodiments.

FIG. 1 illustrates a wired ultrasound system 100 in accordance with some embodiments. FIG. 3 illustrates a block diagram of the wired ultrasound system 100 in accordance with some embodiments.

As shown, the wired ultrasound system 100 includes a console 102, a display 104, and a wired ultrasound probe 106. During operation of the wired ultrasound system 100, the articulating probe head 132 of the wired ultrasound probe 106 is placed against skin of a patient. An ultrasound beam is produced so as to ultrasonically image a portion of a target such as a blood vessel beneath a surface of the skin of the patient. The ultrasonic image of the blood vessel can be depicted on the display screen of the display 104 along with the measured pressure values as set forth below. The wired ultrasound system 100 is useful for assessing access sites such as assessing a blood vessel within a body of a patient before making a percutaneous puncture with a needle to place a VAD such as a catheter into the blood vessel. The wired ultrasound system 100 is also useful for assessing access sites subsequent to placing VADs. However, it should be appreciated that the wired ultrasound system 100 can be useful in a variety of ultrasound-based medical procedures other than catheterization. For example, the percutaneous puncture with the needle can be performed to biopsy tissue of an organ of the patient.

The console 102 houses a variety of components of the wired ultrasound system 100, and it is appreciated the console 102 can take any of a variety of forms. A processor 108 and memory 110 such as random-access memory ("RAM") or non-volatile memory (e.g., electrically erasable programmable read-only memory ["EEPROM"]) is included in the console 102 for controlling various functions of the wired ultrasound system 100, as well as executing various logic operations or algorithms via logic 112 during operation of the wired ultrasound system 100 in accordance with executable instructions 114 therefor stored in the memory 110 for execution by the processor 108. For example, the console 102 is configured to instantiate by way of the instructions 114 one or more processes for controlling the functions of the wired ultrasound system 100, processing electrical signals from the ultrasonic transducers 140 of the wired ultrasound probe 106 into ultrasound images, processing electrical signals from the pressure-sensing device of the wired ultrasound probe 106 into measured pressure values, etc. A digital controller/analog interface 116 is also included with the console 102 and is in communication with both the processor 108 and other system components to govern interfacing between the wired ultrasound probe 106 and other system components set forth herein.

A controller of the console 102, optionally implemented between the processor 108 and the memory 110 of the console 102, is communicatively coupled to the pressure-sensing device 134 of the wired ultrasound probe 106 set forth below. The controller is configured to convert electrical signals corresponding to deformations of the boot 138 of the wired ultrasound probe 106 into measured pressure values, the deformations being those in or around the elastic material of the boot 138 induced by pressing the articulating probe head 132 into a patient. Notably, the logic 112 of the console 102 is configured to compare each measured pressure value against a threshold pressure value to alert a clinician when a measured pressure value exceeds the threshold pressure value. For example, the console 102 can include a speaker configured to emit an audio signal to alert the clinician when the measured pressure value exceeds the threshold pressure value. In another example, the display 104 is configured to emit a visual signal on the display screen to alert a clinician when the measured pressure value exceeds the threshold pressure value.

The wired ultrasound system 100 further includes ports 118 for connection with additional components such as optional components including a printer, storage media, a keyboard, etc. The ports 118 can be universal serial bus ("USB") ports, though other types of ports can be used for this connection or any other connections shown or described herein.

A power connection 120 is included with the console 102 to enable an operable connection to an external power supply 122. An internal power supply 124 (e.g., a battery) can also be employed either with or exclusive of the external power supply 122. Power management circuitry 126 is included with the digital controller/analog interface 116 of the console 102 to regulate power use and distribution.

The display 104 includes a display screen integrated into the console 102 to provide a graphical user interface ("GUI"), render one or more ultrasound images of the target (e.g., the blood vessel) attained by the wired ultrasound probe 106, and display 104 any related information such as the measured pressure values for the articulating probe head 132 when attaining the one-or-more ultrasound images. In addition, the display 104 can be configured to display visual feedback including a visualization of a target (e.g., a blood vessel such as a vein) and a VAD such as a catheter placed in the target. Notwithstanding the foregoing, the display 104 can alternatively be separate from the console 102 and communicatively coupled thereto. Control buttons (see FIG. 1) accessed through a console button interface 128 of the console 102 can be used to immediately call up a desired mode of the wired ultrasound system 100 to the display screen for assistance in an ultrasound-based medical procedure such as assessing the foregoing target or placing a VAD therein.

The wired ultrasound probe 106 is employed in connection with ultrasound-based visualization of a target such as a blood vessel in preparation for placing a VAD such as a catheter into the target. Such visualization gives real-time ultrasound guidance and assists in reducing complications commonly associated with VAD placement such as catheter extravasation. The wired ultrasound probe 106 is configured to provide to the console 102 electrical signals from the ultrasonic transducers 140 of the wired ultrasound probe 106, electrical signals from the pressure-sensing device of the wired ultrasound probe 106, or a combination thereof for real-time ultrasound guidance in VAD placement or other medical procedures.

FIGS. 1 and 7-11 illustrate various views of the wired ultrasound probe 106 in accordance with some embodiments.

As shown, the wired ultrasound probe 106 includes a probe body 130, an articulating probe head 132 attached to the probe body 130, and a pressure-sensing device 134 housed in an articulating area 136 between the articulating probe head 132 and the probe body 130. The wired ultrasound probe 106 further includes a boot 138 connecting the articulating probe head 132 to the probe body 130 in the articulating area 136. The boot 138 is configured to cover or incorporate therein the pressure-sensing device 134.

The articulating probe head 132 houses an array of ultrasonic transducers 140, wherein the ultrasonic transducers 140 are piezoelectric ultrasonic transducers or capacitive micromachined ultrasonic transducers ("CMUTs"). The articulating probe head 132 is configured for placement against skin of a patient proximate a prospective VAD placement site where the ultrasonic transducers 140 in the articulating probe head 132 can generate and emit the generated ultrasound signals into the patient in a number of pulses, receive reflected ultrasound signals or ultrasound echoes from the patient by way of reflection of the generated ultrasonic pulses by the body of the patient, and convert the reflected ultrasound signals into corresponding electrical signals for processing into ultrasound images by the console 102. In this way, a clinician can employ the wired ultrasound system 100 to determine a suitable VAD placement site and establish vascular access therewith.

The pressure-sensing device 134 is configured to detect deformations in or around an elastic material of the boot 138, which deformations are induced by pressing the articulating probe head 132 into a patient. The pressure-sensing device 134 can be a pressure transducer or a number of pressure transducers. For example, the pressure transducer can be a piezoresistive strain-gauge pressure transducer. Such a pressure transducer includes a strain gauge bonded to a flexible diaphragm in the articulating area 136 between the articulating probe head 132 and the probe body 130. A deformation in the diaphragm provides a corresponding measurable change in strain-gauge electrical resistance indicative of the pressure induced by pressing the articulating probe head 132 into the patient to cause the deformation. In another example, the pressure transducer is a variable capacitance pressure transducer. Such as pressure transducer includes a diaphragm electrode and an opposing electrode in the articulating area 136 between the articulating probe head 132 and the probe body 130. A deformation in a flexible diaphragm affects a distance between the diaphragm electrode and the opposing electrode providing a corresponding measurable change in capacitance indicative of the pressure induced by pressing the articulating probe head 132 into the patient to cause the deformation.

The wired ultrasound probe 106 further includes control buttons 142 for controlling certain aspects of the wired ultrasound system 100 during an ultrasound-based medical procedure, thus eliminating the need for the clinician to reach out of a sterile field around a patient to control the wired ultrasound system 100. For example, the control buttons 142 (see FIG. 7) included on the wired ultrasound probe 106 can be used to immediately call up a desired mode to the display screen by the clinician for assistance in VAD placement or some other an ultrasound-based medical procedure.

FIG. 3 shows that the wired ultrasound probe 106 further includes a button-and-memory controller 144 for governing button and ultrasound-probe operation. The button-and-memory controller 144 can include non-volatile memory (e.g., EEPROM). The button-and-memory controller 144 is in operable communication with a probe interface 146 of the console 102, which includes an input/output ("I/O") component 148 for interfacing with the ultrasonic transducers 140 and a button and memory I/O component 150 for interfacing with the button-and-memory controller 144.

Figure 5:
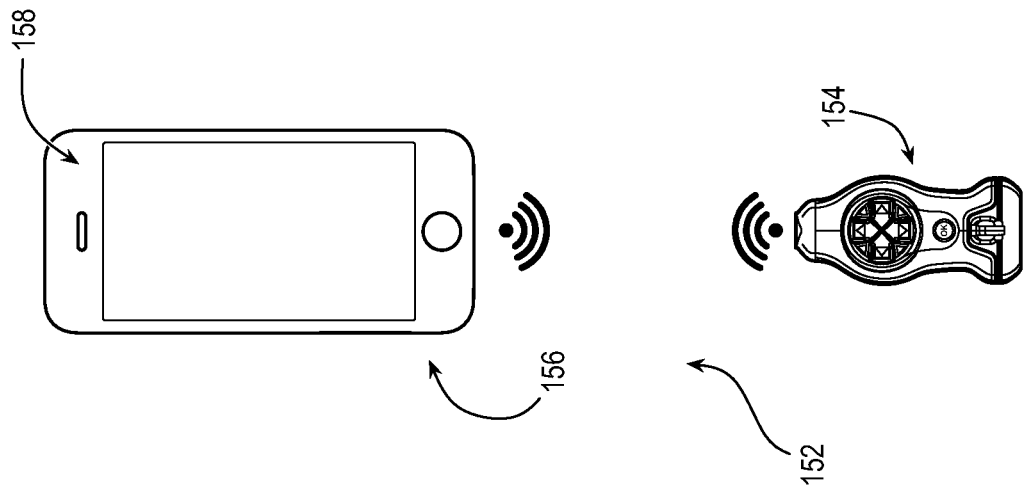
FIG. 5 illustrates a wireless ultrasound system including a companion device and an ultrasound probe in accordance with some embodiments.
Figure 4:
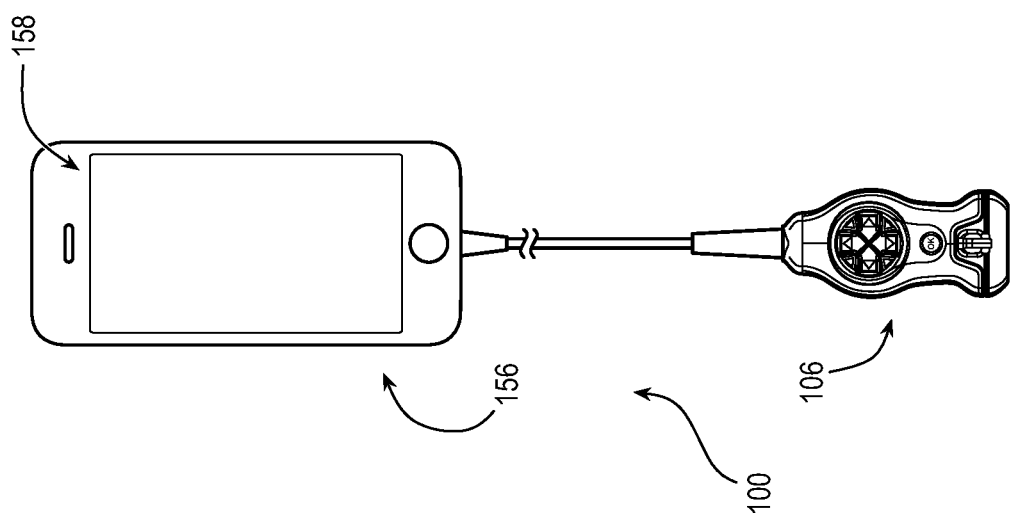
FIG. 4 illustrates a wired ultrasound system including a companion device and an ultrasound probe in accordance with some embodiments.

FIGS. 2 and 5 illustrate a wireless ultrasound system 152 in accordance with some embodiments. FIG. 4 illustrates the wired ultrasound system 100 in accordance with some other embodiments than those set forth above; indeed, the wired ultrasound probe 106 shown in FIG. 4 is like the wireless ultrasound probe 154 in that the processing of the electrical signals from the ultrasonic transducers 140 and the pressure-sensing device 134 of the wired ultrasound probe 106 is by the wired ultrasound probe 106, itself, for display on the companion device 156 through a wired connection instead of a wireless connection. FIG. 3 illustrates a block diagram of the wireless ultrasound system 152 in accordance with some embodiments.

While description of the wireless ultrasound system 152 is set forth below, it should be understood that the wireless ultrasound system 152 includes similar components to the wired ultrasound system 100 set forth above, albeit distributed differently about the wireless ultrasound system 152. For example, the wireless ultrasound probe 154, itself, can include the processor 108, the memory 110, the instructions 114, and the logic 112 of the console 102 for controlling various functions of the wireless ultrasound probe 154, converting electrical signals corresponding to deformations in or around the boot 138 of the wireless ultrasound probe 154 into measured pressure values, processing electrical signals from the ultrasonic transducers 140 into ultrasound-image data or files, and the like. Notwithstanding the foregoing, the companion device 156 (e.g., the console 102 of FIG. 2 or the smartphone, phablet, or tablet of FIGS. 4 and 5) still includes a processor, memory, instructions, logic, etc.; however, such components need not be configured for processing electrical signals from the ultrasonic transducers 140 into ultrasound-image data or files, for example. Indeed, such components can instead be configured to display ultrasound images corresponding to the ultrasound-image data or files provided by the wireless ultrasound probe 154.

As shown, the wireless ultrasound system 152 includes a wireless ultrasound probe 154 and a companion device 156 such as the smartphone, phablet, or tablet of FIGS. 4 and 5 or, in some embodiments, the console 102 of FIG. 2. The companion device 156 includes a display 158 and a wireless module 160 configured for wireless communications with the wireless ultrasound probe 154 and, optionally, a remote Electronic Health Record ("EHR") system. During operation of the wireless ultrasound system 152, the articulating probe head 132 of the wireless ultrasound probe 154 is placed against skin of a patient. An ultrasound beam is produced so as to ultrasonically image a portion of a target such as a blood vessel beneath a surface of the skin of the patient. The ultrasonic image of the blood vessel can be depicted on a display screen of the display 158 of the companion device 156 along with the measured pressure values by wirelessly providing data corresponding thereto from the wireless ultrasound probe 154 to the companion device 156. The wireless ultrasound system 152 is useful for assessing a target such as a blood vessel within a body of a patient before making a percutaneous puncture with a needle to place a VAD such as a catheter into the blood vessel. However, it should be appreciated that the wireless ultrasound system 152 can be useful in a variety of ultrasound-based medical procedures other than catheterization. For example, the percutaneous puncture with the needle can be performed to biopsy tissue of an organ of the patient.

FIGS. 7-11 illustrate various views of the wired ultrasound probe 106 in accordance with some embodiments; however, the wired ultrasound probe 106 and the wireless ultrasound probe 154 share at least the features as set forth below.

As shown, the wireless ultrasound probe 154 includes the probe body 130, the articulating probe head 132 attached to the probe body 130, and the pressure-sensing device 134 housed in the articulating area 136 between the articulating probe head 132 and the probe body 130. The wired ultrasound probe 106 further includes the boot 138 connecting the articulating probe head 132 to the probe body 130 in the articulating area 136. The boot 138 is configured to cover or incorporate therein the pressure-sensing device 134. The wireless ultrasound probe 154 with the articulating probe head 132 is capable of vein and catheter visualization. Like the wired ultrasound probe 106 set forth above, the wireless ultrasound probe 154 depicted in FIGS. 7-11 can be used for assessing access sites before and after placement of VADs.

The probe body 130 houses a printed circuit board assembly ("PCBA") 162. The PCBA 162 includes a number of electronic components of the wireless ultrasound probe 154 shown in the block diagram thereof. (See FIG. 6.) The PCBA 162 is communicatively coupled to control buttons 142 including a power button configured for toggling power to the wireless ultrasound probe 154 from power source 163 (e.g., internal battery) and various other buttons for operation of the wireless ultrasound probe 154.

Like the articulating probe head 132 of the wired ultrasound probe 106, the articulating probe head 132 of the wireless ultrasound probe 154 houses the array of ultrasonic transducers 140, wherein the ultrasonic transducers 140 are piezoelectric ultrasonic transducers or CMUTs. Again, the articulating probe head 132 is configured for placement against skin of a patient proximate a prospective VAD placement site where the ultrasonic transducers 140 in the articulating probe head 132 can generate and emit the generated ultrasound signals into the patient in a number of pulses, receive reflected ultrasound signals or ultrasound echoes from the patient by way of reflection of the generated ultrasonic pulses by the body of the patient, and convert the reflected ultrasound signals into corresponding electrical signals for processing into ultrasound images by the wireless ultrasound probe 154.

Further like the wired ultrasound probe 106, the pressure-sensing device 134 of the wireless ultrasound probe 154 is configured to detect deformations in or around the elastic material of the boot 138, which deformations are induced by pressing the articulating probe head 132 into a patient. The pressure-sensing device 134 can be a pressure transducer or a number of pressure transducers placed in the articulating area 136 between the probe body 130 and the articulating probe head 132. As set forth above, the pressure transducer can be a piezoresistive strain-gauge pressure transducer including a strain gauge bonded to a flexible diaphragm in the articulating area 136 between the articulating probe head 132 and the probe body 130. As further set forth above, the pressure transducer can be a variable capacitance pressure transducer including a diaphragm electrode and an opposing electrode in the articulating area 136 between the articulating probe head 132 and the probe body 130.

The pressure-sensing device 134 is communicatively coupled to a controller of the wireless ultrasound probe 154, which controller is optionally implemented between the processor 166 and the memory 168 of the wireless ultrasound probe 154. (See FIG. 6.) The controller is configured to convert electrical signals corresponding to the deformations in or around the elastic material of the boot 138 into the measured pressure values. The wireless ultrasound probe 154 is configured to provide the measured pressure values to the companion device 156 to be displayed to a clinician on the display screen of the companion device 156.

Notably, the wireless ultrasound probe 154 includes logic 164 configured to compare a measured pressure value against a threshold pressure value. Should the measured pressure value exceed the threshold pressure value, the wireless ultrasound probe 154 can send an electrical signal to the companion device 156 to visually or audibly alert a clinician to the foregoing measured pressure value over the threshold value. The wireless ultrasound probe 154 can additionally or alternatively include a speaker configured to emit an audio signal to alert the clinician when the measured pressure value exceeds the threshold pressure value. Additionally or alternatively, the wireless ultrasound probe 154 can include a light-emitting diode configured to emit a visual signal to alert the clinician when the measured pressure value exceeds the threshold pressure value. In this way, the wireless ultrasound probe 154 can be used to detect and determine if bodily tissue is over-compressed during ultrasound imaging. Notably, if a patient possesses excess adipose tissue, the adipose tissue can appreciably compress under the pressure induced by the articulating probe head 132. This can allow for a larger portion of, for example, a catheter to be advanced into a blood vessel. However, when the pressure induced by the articulating probe head 132 is removed, the adipose tissue can rebound causing some of the catheter to be extracted, thereby reducing the catheter purchase length. This can lead to catheter extravasation. Once the clinician is alerted of the pressure exceeding the threshold value, the clinician can check the catheter for correct placement inside the blood vessel to avoid catheter extravasation.

Figure 6:
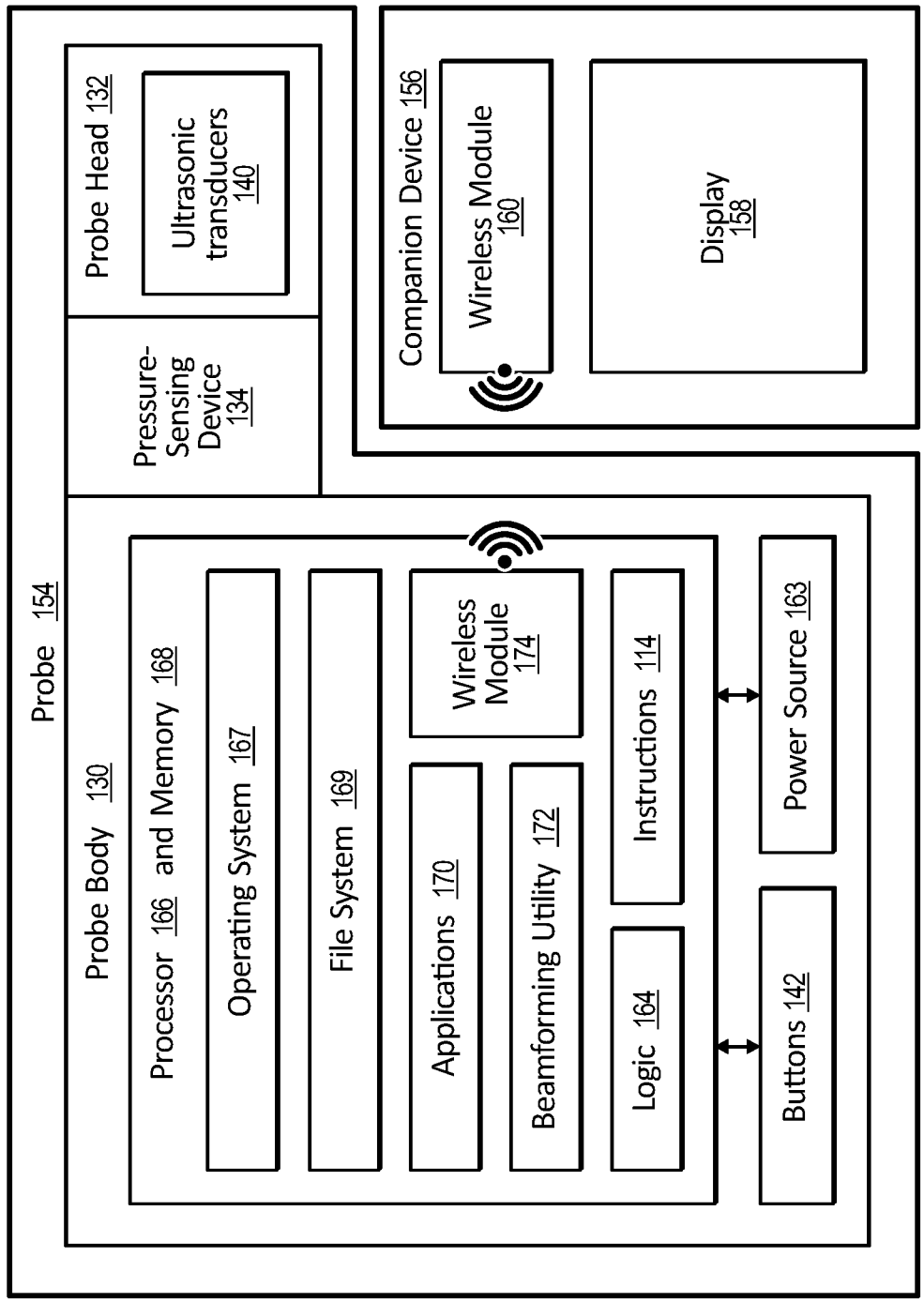
FIG. 6 illustrates a block diagram of the ultrasound system of FIG. 2, FIG. 4, or 5 in accordance with some embodiments.
Figure 7:
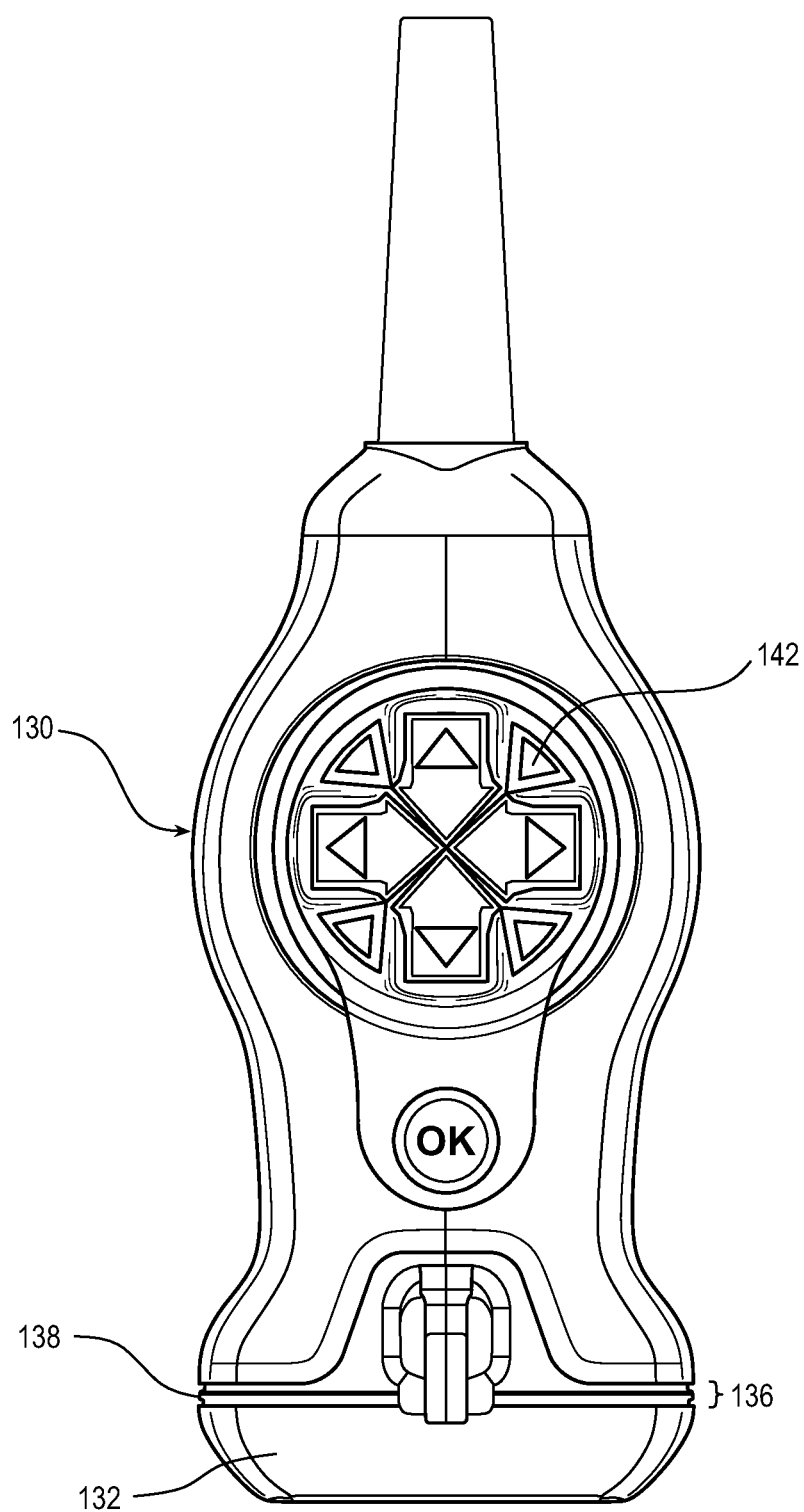
FIG. 7 illustrates a front view of an ultrasound probe including a pressure-sensing device in accordance with some embodiments.
Figure 8:
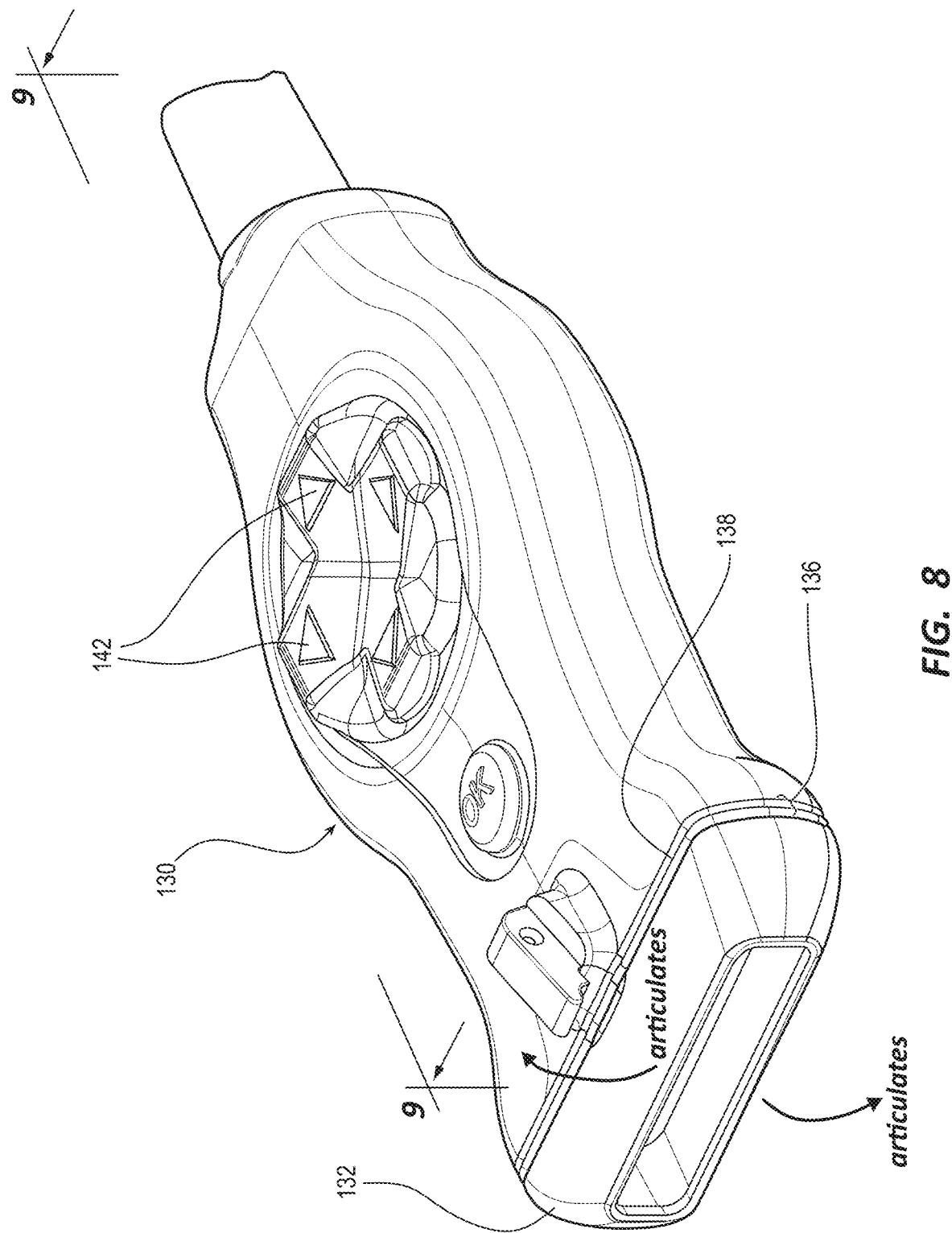
FIG. 8 illustrates a perspective view of the ultrasound probe in accordance with some embodiments.
Figure 9:
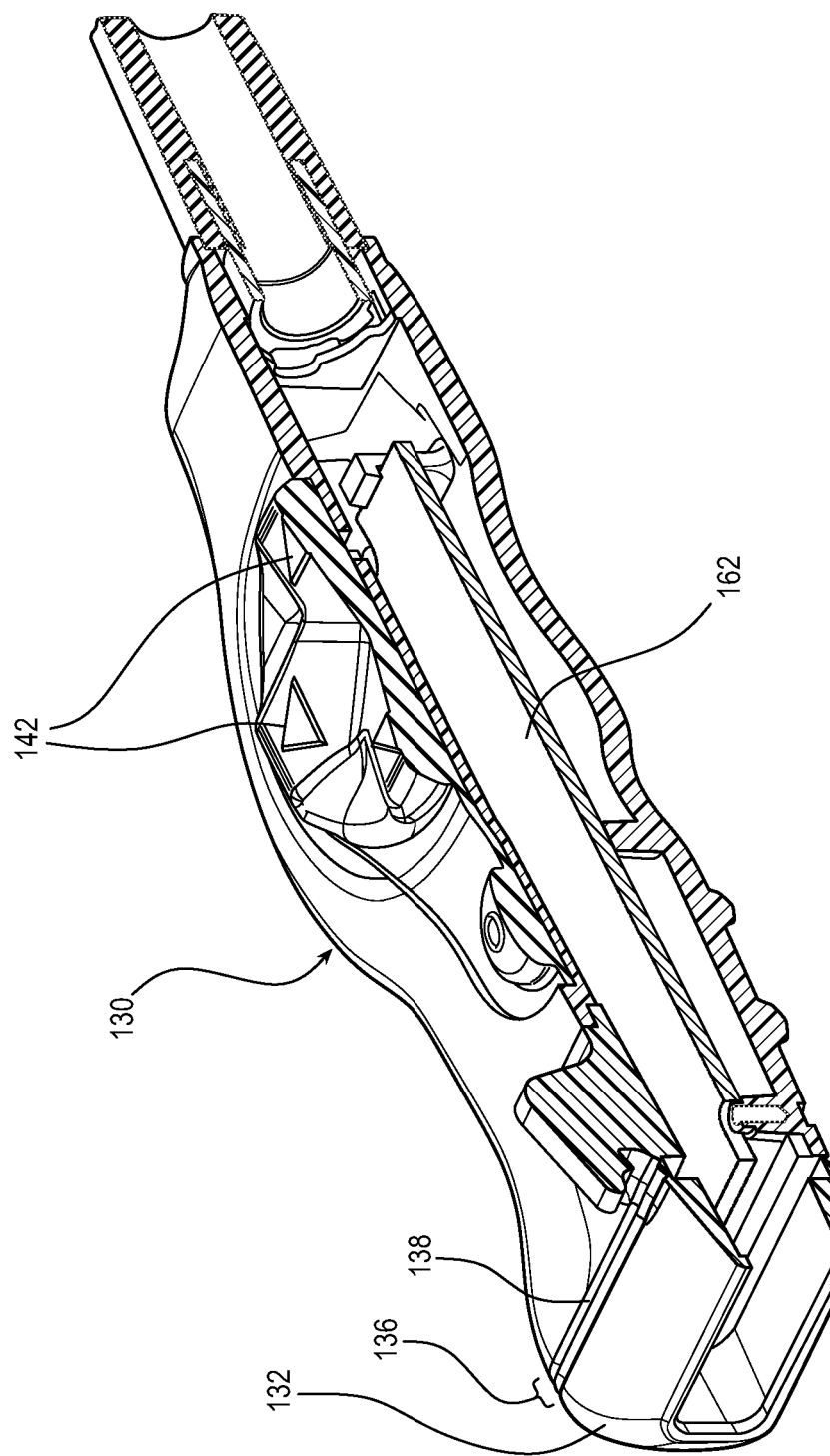
FIG. 9 illustrates a cross section of the ultrasound probe in accordance with some embodiments.
Figures 10, 11:
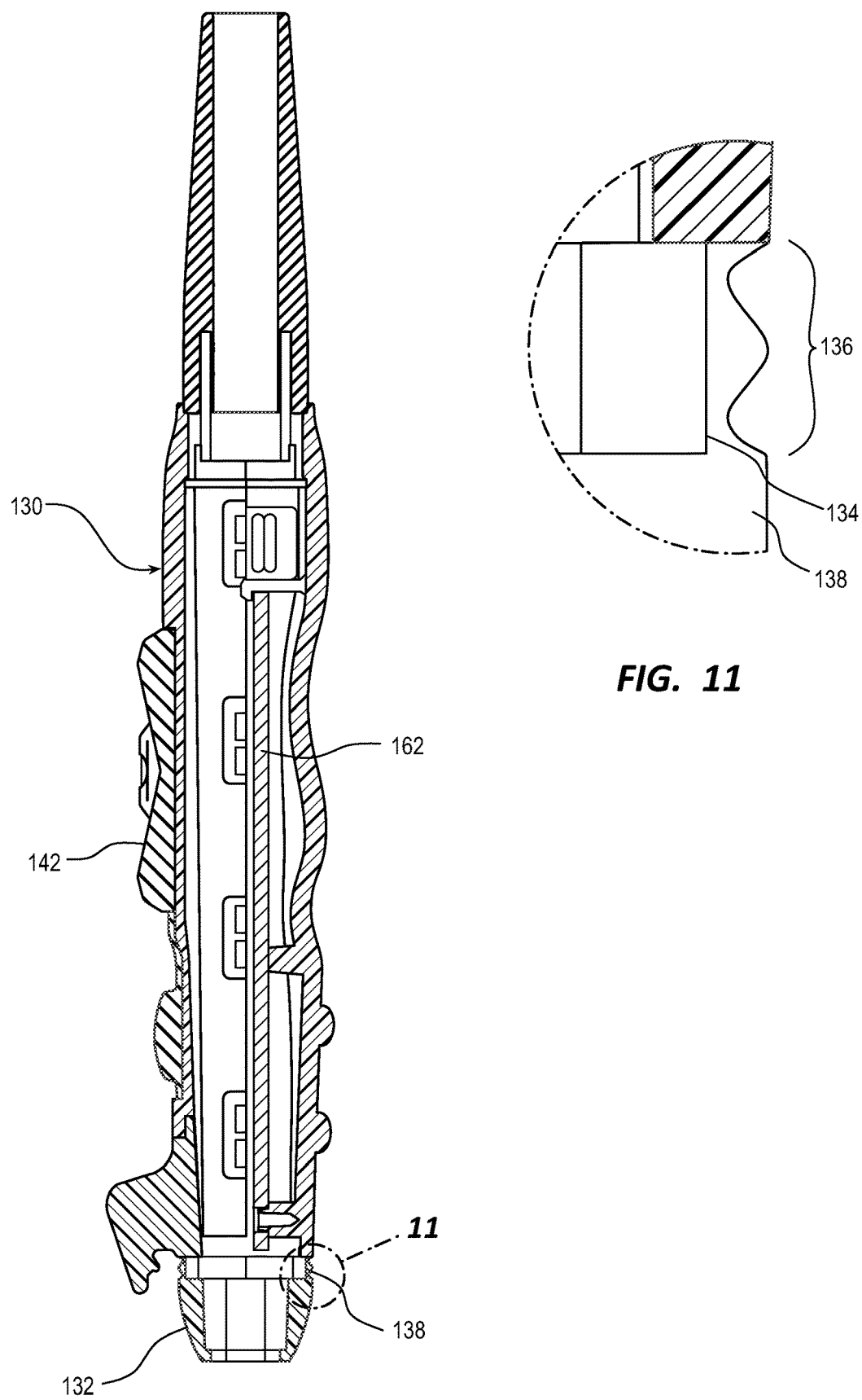
FIG. 10 illustrates another cross section of the ultrasound probe in accordance with some embodiments.
FIG. 11 illustrates a detailed view of an articulating area of the ultrasound probe including the pressure-sensing device in accordance with some embodiments.

FIG. 6 illustrates a block diagram of the wireless ultrasound system 152 in accordance with some embodiments.

As shown, the wireless ultrasound probe 154 includes a processor 166 for governing system functionality by employment of a general-purpose operating system 167, memory 168 including a file system 169, and applications 170 that can be stored in the memory 168 and executed by the processor 166. Some of the applications 170 can provide a user interface to allow a clinician to monitor the pressure induced on a patient by the articulating probe head 132. A beamforming utility 172, including suitable circuitry is also controlled by the processor 166 to enable signals to be produced, received, and further processed. For example, the beamforming utility 172 produces electrical signals received by the ultrasonic transducers 140 in the articulating probe head 132. The articulating probe head 132 passes ultrasound signals corresponding to the electrical signals into an area of a patient and receives reflected ultrasound signals from the patient. The reflected ultrasound signals, in turn, are converted into corresponding electrical signals by the ultrasonic transducers 140 in the articulating probe head 132, which electrical signals are provided to the beamforming utility 172 for further processing into ultrasound-image data or files for display on the companion device 156. Note that the wireless ultrasound probe 154 can include different components such as more or fewer components than those set forth herein, including those components such as the wireless module 174 that enable the wireless ultrasound probe 154 to operate in a wireless manner with the companion device 156.

The wired or wireless ultrasound system 100 or 152 with the integrated pressure-sensing device 134 provides versatility beyond vein visualization for VAD placement as set forth above. Having a wired or wireless ultrasound system 100 or 152 that not only provides for ultrasound imaging but ensures that the application of the wired or wireless ultrasound probe 106 or 154 against a patient's skin does not result in excessive pressure induced by the articulating probe head 132, advantageously reduces a risk of catheter extravasation.

Methods

Methods include a method of using the wired or wireless ultrasound system 100 or 152. For example, the method includes one or more steps selected from an ultrasound probe-obtaining step, an ultrasound probe-placing step, an ultrasound probe-moving step, a pressure-monitoring step, and a catheter placement-adjusting step.

The ultrasound probe-obtaining step includes obtaining the wired or wireless ultrasound probe 106 or 154. As set forth above, the wired and wireless ultrasound probes 106 and 154 include the probe body 130, the articulating probe head 132 attached to the probe body 130, and the pressure-sensing device 134 housed in the articulating area 136 between the articulating probe head 132 and the probe body 130.

The ultrasound probe-placing step includes placing the articulating probe head 132 of the wired or wireless ultrasound probe 106 or 154 on a skin surface of a patient.

The ultrasound probe-moving step includes moving the articulating probe head 132 of the wired or wireless ultrasound probe 106 or 154 over the patient while ultrasound signals are emitted into the patient from the articulating probe head 132 for ultrasound imaging.

The pressure-monitoring step includes monitoring for any measured pressure values induced on the patient by the articulating probe head 132 of the ultrasound probe in excess of a threshold pressure value. The monitoring can include viewing the measured pressure values on the display screen of the display 104 of the console 102 or the display 158 of the companion device 156. Such monitoring can also include monitoring for an audio signal or a visual signal on the display screen of the display 104 or 158. Such signals alert a clinician when any measured pressure values are in excess of the threshold pressure value.

The method further includes a catheter placement-adjusting step. The catheter placement-adjusting step includes adjusting catheter placement responsive to any measured pressure values in excess of the threshold pressure value to ensure a sufficient blood-vessel purchase by the catheter that minimizes catheter extravasation.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures can be made from the particular embodiments disclosed herein without departing from the scope of the concepts provided herein.

What is claimed is:

1. An ultrasound probe, comprising:
   a probe body configured to be supported by a clinician and for external use on a patient;
   an articulating probe head including one or more ultrasonic transducers, and attached to the probe body, the articulating probe head configured to be placed on a skin surface of the patient, and configured to articulate relative to the probe body; and
   a pressure-sensing device housed in an articulating area between the articulating probe head and the probe body.

2. The ultrasound probe of claim 1, further comprising a boot connecting the articulating probe head to the probe body in the articulating area, the boot configured to cover or incorporate therein the pressure-sensing device.

3. The ultrasound probe of claim 2, wherein the pressure-sensing device is configured to detect deformations in or around an elastic material of the boot induced by pressing the articulating probe head into the patient.

4. The ultrasound probe of claim 3, wherein the pressure-sensing device is communicatively coupled to a controller of the ultrasound probe configured to convert electrical signals corresponding to the deformations into measured pressure values.

5. The ultrasound probe of claim 4, wherein the ultrasound probe is configured to provide the measured pressure values to a display to be displayed to the clinician.

6. The ultrasound probe of claim 1, wherein the ultrasound probe includes logic configured to compare a measured pressure value from the pressure-sensing device against a threshold pressure value.

7. The ultrasound probe of claim 6, wherein the ultrasound probe includes a speaker configured to emit an audio signal to alert the clinician when the measured pressure value exceeds the threshold pressure value.

8. The ultrasound probe of claim 6, wherein the ultrasound probe includes a light-emitting diode configured to emit a visual signal to alert the clinician when the measured pressure value exceeds the threshold pressure value.

9. The ultrasound probe of claim 1, wherein the pressure-sensing device is a pressure transducer.

10. The ultrasound probe of claim 9, wherein the pressure transducer is a piezoresistive strain-gauge pressure transducer including a strain gauge bonded to a flexible diaphragm in the articulating area between the articulating probe head and the probe body, a deformation in the flexible diaphragm providing a corresponding measurable change in strain-gauge electrical resistance indicative of pressure induced by pressing the articulating probe head into the patient to cause the deformation.

11. The ultrasound probe of claim 9, wherein the pressure transducer is a variable capacitance pressure transducer including a diaphragm electrode and an opposing electrode in the articulating area between the articulating probe head and the probe body, a deformation in a flexible diaphragm affecting a distance between the diaphragm electrode and the opposing electrode providing a corresponding measurable change in capacitance indicative of pressure induced by pressing the articulating probe head into the patient to cause the deformation.

12. An ultrasound system, comprising:
a console including a display configured for rendering ultrasound images on a display screen of the display; and
an ultrasound probe including:
a probe body configured to be supported by a clinician and for external use on a patient;
an articulating probe head including one or more ultrasonic transducers, and attached to the probe body, the articulating probe head configured to be placed on a skin surface of the patient, and configured to articulate relative to the probe body; and
a pressure-sensing device housed in an articulating area between the articulating probe head and the probe body.

13. The ultrasound system of claim 12, the ultrasound probe further comprising a boot connecting the articulating probe head to the probe body in the articulating area, the boot configured to cover or incorporate therein the pressure-sensing device.

14. The ultrasound system of claim 13, wherein the pressure-sensing device is configured to detect deformations in or around an elastic material of the boot induced by pressing the articulating probe head into the patient.

15. The ultrasound system of claim 14, wherein the pressure-sensing device is communicatively coupled to a controller of the console configured to convert electrical signals corresponding to the deformations into measured pressure values.

16. The ultrasound system of claim 15, wherein the ultrasound probe is configured to provide the measured pressure values to the display to be displayed to the clinician.

17. The ultrasound system of claim 12, wherein the console includes logic configured to compare a measured pressure value from the pressure-sensing device against a threshold pressure value.

18. The ultrasound system of claim 17, wherein the console includes a speaker configured to emit an audio signal to alert the clinician when the measured pressure value exceeds the threshold pressure value.

19. The ultrasound system of claim 17, wherein the display is configured to emit a visual signal to alert the clinician when the measured pressure value exceeds the threshold pressure value.

20. The ultrasound system of claim 12, wherein the display is configured to display visual feedback including a visualization of a target vein and a catheter placed in the target vein.

21. The ultrasound system of claim 12, wherein the pressure-sensing device is a piezoresistive strain-gauge pressure transducer including a strain gauge bonded to a flexible diaphragm in the articulating area between the articulating probe head and the probe body, a deformation in the flexible diaphragm providing a corresponding measurable change in strain-gauge electrical resistance indicative of pressure induced by pressing the articulating probe head into the patient to cause the deformation.

22. The ultrasound system of claim 12, wherein the pressure-sensing device is a variable capacitance pressure transducer including a diaphragm electrode and an opposing electrode in the articulating area between the articulating probe head and the probe body, a deformation in a flexible diaphragm affecting a distance between the diaphragm electrode and the opposing electrode providing a corresponding measurable change in capacitance indicative of pressure induced by pressing the articulating probe head into the patient to cause the deformation.

* * * * *